United States Patent [19]

Merten et al.

[11] 4,187,248
[45] Feb. 5, 1980

[54] MAKING A NITRODIARYLAMINE BY REACTING AN ALKALI METAL SALT OF A FORMAMIDE WITH A NITROHALOARENE

[75] Inventors: Helmut L. Merten, Hudson; Gene R. Wilder, Medina, both of Ohio

[73] Assignee: Monsanto Company, St. Louis, Mo.

[21] Appl. No.: 854,109

[22] Filed: Nov. 23, 1977

[51] Int. Cl.$^2$ .............................................. C07C 85/20
[52] U.S. Cl. ..................................... 260/576; 260/571
[58] Field of Search ..................... 260/576, 562 R, 571

[56] References Cited

U.S. PATENT DOCUMENTS

| | | | |
|---|---|---|---|
| 1,882,759 | 10/1932 | Britton et al. | 260/576 |
| 2,442,952 | 6/1948 | Kitchens | 260/562 R |
| 3,099,689 | 7/1963 | Cragg | 260/562 R X |

OTHER PUBLICATIONS

Rondestvedt, "J. Org. Chem.", vol. 42 (10), pp. 1786–1790, (1977).
Kothnig et al., "Chem. Ab.", vol. 54, Ab. No. 3205i, (1960).

*Primary Examiner*—John Doll
*Attorney, Agent, or Firm*—Gordon B. Seward

[57] ABSTRACT

Preparation of a nitrodiarylamine from a nitrohaloarene and alkali metal salt of the formyl derivative of a primary aromatic amine is disclosed.

14 Claims, No Drawings

4,187,248

MAKING A NITRODIARYLAMINE BY REACTING AN ALKALI METAL SALT OF A FORMAMIDE WITH A NITROHALOARENE

MAKING NITRODIARYLAMINES

The invention relates to the preparation of nitrodiarylamines which are valuable intermediates for the preparation of dyestuffs and antidegradants. For example, 4-nitrodiphenylamine is an important intermediate for rubber antidegradants. The invention particularly relates to the preparation of

BACKGROUND OF THE INVENTION

It is known to form nitrodiarylamines from nitrohaloarenes and N-acylaromatic amines or other activated form of the amine in the presence of a so-called acid acceptor for which purpose potassium carbonate is commonly used. For reasons which have not heretofore been explained, sodium carbonate gives inferior results. The process suffers from the disadvantages, among others, that large amounts of inorganic salts are required and large amounts of by-products are formed. The disposal of by-products creates an environmental problem. A process has now been discovered which reduces the amount of inorganic material required, minimizes side reactions and reduces the load on the environment.

SUMMARY OF THE INVENTION

In accordance with this invention, nitrodiarylamine is formed by reacting the nitrohaloarene with an alkali metal derivative of an N-formylaromatic amine, the alkali metal of which has an atomic number greater than lithium in the periodic arrangement of the elements. Such alkali metal derivatives are presumed to be salts and are hereinafter so designated.

Having an N-formylaromatic amine in the reaction mixture with the alkali metal salt gives optimum results; and, in the case of the sodium salt, is required in amount of at least about 0.4 mole per mole of nitrohaloarene. The salt need not be isolated prior to reaction; but, as hereinafter demonstrated, may be preformed in the molar quantity required in a suitable reaction medium and reacted with nitrohaloarene. However, the quality of the salt is of the utmost importance for good results in reaction with nitrohaloarene. For example, it should be essentially free of bound water and alcohol.

In one embodiment of the invention, the nitrodiarylamine is formed by reacting nitrohaloarene with a potassium, cesium or rubidium salt of an N-formyl aromatic amine. The aforesaid salts have special properties. The sodium salt is more sluggish in reaction, gives lower quality products and higher quantities of by-products. For example, in refluxing xylene, the reaction rate of potassium formanilide with p-nitrochlorobenzene is about twenty times that observed with sodium formanilide. The lithium salt is unreactive in non-polar solvents under comparable conditions.

For the reaction of p-nitrochlorobenzene and a salt of formanilide, the potassium salt is preferred in a molar ratio of about 1.0 to 1.5 moles per mole of p-nitrochlorobenzene; and, more preferably, 1.2 to 1.4 moles. It is also preferred that in addition to the potassium salt, formanilide be present in the reaction mixture. The molar amount of formanilide charged may be equal to or greater than the molar amount of potassium formanilide; but, to minimize recovery problems and maximize production per unit volume, lower amounts are advantageous. The preferred range is 0.2–0.7 mole of formanilide per mole of p-nitrochlorobenzene; and, more preferably, 0.4–0.5 mole. The formanilide serves as polar solvent and reaction promoter. The reaction goes readily at a temperature of 140°–180° C. The preferred reaction temperature is 155°–165° C. An important advantage of the potassium salt is that the reaction can be conducted at temperatures below those heretofore feasible. It will be understood that the process is not limited to the aforesaid temperatures and may be conducted at either lower or higher temperatures; for example, 110°–210° C., and in some embodiments, the higher temperatures are preferred.

The present invention renders complete conversion of p-nitrochlorobenzene feasible whereas heretofore, it has been advantageous to recycle excess para-nitrochlorobenzene because the formation of by-products became excessive when all of the p-nitrochlorobenzene was converted.

For the reaction of potassium, cesium and rubidium salts, the use of a solvent is not essential, but is desirable. A solvent may serve to control the reaction temperature, dissolve the salt reactant or, in the case of polar solvents, actually to promote the reaction. Use of mixtures of polar and nonpolar solvents is often advantageous. The process is operative with inert non-polar solvents such as xylene, cumene, or diisopropylbenzene and polar solvents such as: 1,2-bis-2-methoxyethoxyethane, dimethylformamide and dimethylsulfoxide. However, the aforesaid polar solvents are expensive and not entirely inert but subject to loss from reaction involving the solvent as well as loss on recovery. Presence of a polar solvent is advantageous; and it is much preferred to use the formyl derivative corresponding to the salt to be reacted as a polar solvent reaction promoter because the former is also a precursor for the desired product so that any consumption due to reaction is not loss. Also, the formyl derivatives of aromatic primary amines inhibit further reaction of the desired nitrodiarylamine to tertiary amine by-product and serve as solvents for the salts. The formyl derivative of an aromatic primary amine different from the one used to form the salt may be used if a mixture of nitrodiarylamine products is desired. Under the conditions for reacting the alkali metal salts of formyl derivatives of aromatic primary amines neither alcohols nor water can be considered inert solvents. Alcohols have been observed to react with the nitrohaloarene to form significant quantities of the corresponding alkyl nitroaryl ether. Also, the alkali metal salts are subject to hydrolysis in the presence of water.

According to another embodiment of the invention, a feasible process for condensing the economically advantageous sodium salts has been discovered by application of the aforedescribed principles for optimizing the reaction with the potassium salt. The sodium salt is activated by sufficiently high proportions of the formyl derivatives of an aromatic amine whereby good yields are obtained without resorting to expensive special polar solvents such as dimethylformamide. In fact, the results are unexpectedly superior.

Experimental evidence from differential scanning colorimetry indicates that the alkali metal formanilides, or at least those of atomic number above lithium, form adducts with formanilide. The formation of such a complex is undoubtedly significant for the reaction of sodium formanilide with p-nitrochlorobenzene. Sodium formanilide melts much higher than potassium formanilide but the formation of a complex with formanilide appears to lower the melting point and increase the reactivity for reasons as yet obscure. When the ratio of formanilide to p-nitrochlorobenzene is 2, the rate of reaction with sodium formanilide is considerably faster than observed for a corresponding ratio of 1.4. The results imply that solvation of the transition state is extremely important. A non-polar solvent appears to inhibit the rate of solvation of the formanilide-sodium formanilide complex.

In general, for reacting sodium formanilide, formanilide and p-nitrochlorobenzene, it is desirable to use 1.0–1.5 moles of sodium formanilide and 0.4–2.6 moles of formanilide per mole of p-nitrochlorobenzene, preferred proportions being about 1.3 moles of sodium formanilide and about 1.3–1.6 moles of formanilide per mole of p-nitrochlorobenzene. The reaction rates and yields from sodium formanilide are excellent when the mole ratio of formanilide to sodium formanilide is equal to or exceeds 1; preferably 1–2, and the mole ratio of formanilide to p-nitrochlorobenzene is equal to or exceeds 1.3. The reaction temperature will be about 20°–25° C. higher for the sodium salt than for the potassium salt. Any inert solvent, if used, should be kept at a minimum, because of the adverse affect on the reaction rate. The high formanilide level almost eliminates the formation of 4,4'-dinitrotriphenylamine but the amount is increased several fold when dimethylformamide replaces formanilide.

If desired, aniline may be added to reduce carbon monoxide evolution and ultimately decrease formic acid usage. It is believed that aniline traps carbon monoxide by transamidation with N-formyl-p-nitrodiphenylamine intermediate. Thus, the reduction of carbon monoxide is accompanied by conversion of aniline to formanilide.

The alkali metal salts of N-formylaromatic amines may be prepared from the corresponding alkali metal alkoxides in dimethylformamide or xylene. The alcohol is constantly removed to drive the reaction to completion. When xylene is used, a suitable solvent for making sodium salts, the solid salt is allowed to separate under stirring. In dimethylformamide, a solution is present throughout and refractometer readings of the distillate are taken periodically until the refractive index of the higher boiling solvent is obtained.

The method selected for making sodium formanilide may influence the quality of the product and is, of course, determinative of whether the method is acceptable for commercial use in connection with a process of making 4-nitrodiphenylamine. For example, metallic sodium is troublesome and dangerous to handle, liberates explosive hydrogen and, if used in conjunction with recycled material as would ordinarily be necessary in commercial operation, enters into side reactions with resultant increase in by-products and reduction in yield.

A variety of nitrohaloarenes have been proposed for making nitrodiarylamines, any of which appear to be suitable for use in the process of the invention. Illustrative of such nitrohaloarenes are: o-nitrochlorobenzene, o-nitrobromobenzene, p-nitrochlorobenzene, p-nitrobromobenzene, m-nitrochlorobenzene, m-nitrobromobenzene, 1-chloro-2-methyl-4-nitrobenzene, 1-chloro-3-methyl-4-nitrobenzene, 1-chloro-2-nitronaphthalene, 3,4-dichloronitrobenzene, 3-methyl-4-chloronitrobenzene, 2-methyl-4-chloronitrobenzene, 2-ethyl-4-chloronitrobenzene, 2,3-dimethyl 4-chloronitrobenzene, 2,5-dimethyl 4-chloronitrobenzene, 3,5-dimethyl 4-chloronitrobenzene and p-nitrofluorobenzene.

The process is believed to be a general one for condensation of aromatic primary amines as the aforesaid alkali metal salts of the formyl derivatives, but has been examined most extensively with formanilides. Formanilides substituted in the benzene nucleus by one or more substituents inert under the reaction conditions; for example, one or more alkyl, alkoxy, nitro, fluoro or chloro substituents are suitable. Illustrative substituted formanilides which may be used in the process are the alkali metal salts of: 3-chloroformanilide, 4-chloroformanilide, 2-methylformanilide, 3-methylformanilide, 4-methylformanilide, 3-ethylformanilide, 3,4-dimethylformanilide, 3-methoxyformanilide, 4-methoxyformanilide, 4-ethylformanilide, 4-isopropylformanilide, 4-butylformanilide, 3,4-dichloroformanilide and 4-nitroformanilide.

The reaction may be carried out in mild steel, stainless steel, glass or glass-lined vessels. After the condensation reaches the selected end-point, the alkali metal halide byproduct may be removed by water washing; solvent, if present, removed by distillation, and the residue cooled to about 5° C. to recover nitrodiarylamine by crystallization.

DESCRIPTION OF PREFERRED EMBODIMENTS

Example I

Dry Potassium Formanilide

Potassium formanilide believed to be a new compound may be prepared and isolated as follows: From 122 parts by weight (1.3 mole) of 45% potassium hydroxide, 300 parts by weight of butanol and 100 parts by weight of xylene, 1.3 mole of potassium butoxide is prepared by stripping out water into a suitable water trap. The potassium butoxide is then added to a slurry of 156 parts by weight of formanilide in 250 parts by weight of xylene at ambient temperature. The butanol, xylene slurry is distilled in vacuo (100 mm.Hg.) until the overhead refractive index is 1.497, xylene being added to maintain the volume. The slurry is cooled to ambient temperature and the vacuum released under nitrogen. The slurry is then filtered and the xylene replaced by benzene, always keeping a liquid layer over the cake. The benzene is replaced by hexane in the same fashion, the bulk of the hexane is pulled through and the cake quickly transferred to a suitable container and dried. One obtains a crystalline white product soluble in dimethyl formamide, methanol and butanol. Potassium formanilide melts at 184°–186° C. An associated formanilide-K-formanilide adduct melts at 140°–145° C. and some samples of potassium formanilide will show both exotherms in differential scanning calorimetry.

EXAMPLE 2

This example illustrates the preparation of 4-nitrodiphenylamine using, without isolation, potassium formanilide in formanilide made from potassium methylate and illustrates the preparation of the intermediates formanilide and potassium methoxide. The mole ratio is 0.7 mole of formanilide and 1.3 mole of potassium formanilide per mole of p-nitrochlorobenzene.

Formanilide

There are gradually added 58.8 parts by weight of formic acid (97%) to 113.0 parts by weight of aniline while maintaining a temperature of 90°±5° C. After completion of the addition, the mixture is heated at refluxing temperatures for about 25±5 minutes and finally heated to a pot temperature of 170°±5° C. The distillate collected consists of 27.0 parts by weight of water and a very small amount of formic acid (maximum 0.3 parts by weight). To the product in the pot, comprising 142.7 parts by weight of formanilide and 2.2±0.3 parts by weight of aniline, 75.0 parts by weight of xylene is added.

Potassium Methoxide

There are charged to a reactor 153.1 parts by weight of methanol and 66.0 parts by weight of 50% potassium hydroxide and the mixture then heated to boiling. The vapors are introduced into a column suitable to refine aqueous methanol. The water-free methanol is recycled into the reactor. The reaction is complete when a pot sample shows a water content of less than 0.1 wt.%. The resulting product is a 25 wt.% solution of potassium methylate in methanol.

Potassium Formanilide

A reaction mixture is prepared mixing a solution of 184 parts by weight of 25% potassium methylate in methanol (0.65 mole), about 180 parts by weight of xylene and 121 parts by weight (1.0 mole) of formanilide. This mixture is heated in vacuo at 75°–85° C. and the methanol is distilled from the reaction mixture until the refractive index of xylene is obtained. The resulting hot reaction mixture contains about 0.65 molecular proportions of potassium formanilide, and 0.35 molecular proportions of formanilide.

4-Nitrodiphenylamine

To the aforesaid hot reaction mixture of potassium formanilide and formanilide in xylene is added 79.0 parts by weight (0.5 mole) of para-nitrochlorobenzene. The solution is heated to reflux, at a pot temperature of about 142°–143° C. The reaction begins at a pot temperature of about 110°–115° C. as indicated by color change followed by evolution of gas. Heating is continued for about eight hours. The reaction mixture is then cooled to 40° C. while stirring. A yellow solid crystallizes out on standing. There is added 300 parts by weight of water and after stirring the resulting slurry for 0.5 hours, the solids are filtered and washed with xylene. The mother liquor is concentrated to recover a second crop. The yield of 4-nitrodiphenylamine is about 87% and conversion of p-nitrochlorobenzene about 95%. Reaction times can be reduced by reducing the amount of xylene.

The highest yields at minimum reaction temperature are attained from essentially anhydrous potassium formanilide, but small amounts of water have little effect. From a reaction mixture of 31.8 parts by weight (0.2 mole) of dry potassium formanilide, 24.2 parts by weight (0.154 mole) of para-nitrochlorobenzene, 9.3 parts by weight (0.077 mole) of formanilide and 25 parts by weight of xylene there is obtained after heating at 137°–149° C. for about 125 minutes a 92% yield of 4-nitrodiphenylamine and 97% conversion. The addition of 0.5% weight and 1.0% by weight of water respectively based on the potassium formanilide results in little or no reduction in yield and conversion. Addition of 1.0% by weight 45% potassium hydroxide improves the yield slightly. The innocuous effect of a little free water is to be contrasted with the adverse effect of bound water. Potassium formanilide forms a monohydrate which hydrolyzes rapidly when heated above temperatures of 85°–90° C. Replacing about half the formanilide with aniline in the foregoing procedure gives comparable result. The presence of aniline reduces the by-product carbon monoxide about 40% with formation of formanilide by mechanism imperfectly understood.

EXAMPLE 3

This example illustrates the preparation of 4-nitrodiphenylamine using, without isolation, potassium formanilide in formanilide made from potassium butoxide and illustrates the preparation of formanilide using inert solvent recovered from a previous batch and the preparation of potassium butoxide. The mole ratio is 0.5 moles of formanilide and 1.3 moles of potassium formanilide per mole of p-nitrochlorobenzene. The example demonstrates that formanilide, aniline and 4-nitrodiphenylamine can be recycled without changing the course of the reaction.

Formanilide

To 51.2 parts by weight of aniline and 71.6 parts by weight of recovered xylene having a composition of 30.0 parts by weight xylene, 16.3 parts by weight aniline and 25.3 parts by weight formanilide in a suitable reaction vessel is added 34.1 parts by weight of formic acid (97%) gradually while maintaining a maximum temperature of 95° C. After completion of the addition, the mixture is held for about an hour at 90°–95° C. The mixture is then gradually heated to 165°–170° C. The distillate collected consists of 13.8 parts by weight water, 0.1 parts by weight xylene and 2.2 parts by weight aniline formate. The product in the reaction vessel contains 109 parts by weight formanilide, 29.9 parts by weight xylene and 1.8 parts by weight aniline.

Potassium Butoxide

Under a nitrogen blanket, 80.5 parts by weight of 45% potassium hydroxide, 154 parts by weight of 1-butanol and 175 parts by weight of xylene is introduced to a butoxide maker. The butoxide maker is a vessel fitted with an agitator, a two or three plate column and a condenser. The distillate from the column is directed to a phase separator. Heat is applied to the vessel and, as the temperature of the contents of the vessel approaches 105° C., vaporization occurs. The initial boiling point of the vapor at the top of the column is about 80° C. The distillation is carried out as rapidly as practical to maximize water removal. As the distillation proceeds, the pot temperature will rise to 136°±2° C. and the vapor temperature will rise to 116°±3° C. The lower water layer is continuously removed and the upper organic layer is recycled to the top of the column. The distillation is continued until the water content of the reaction mass is below 0.5% as determined by a Karl Fischer titration. The batch is cooled to 50°–60° C. and is now ready for use in the next step.

Potassium Formanilide

The potassium formanilide maker is fitted with an agitator, five-tray column and a vacuum jet. The above-described product comprising 109.0 parts by weight of formanilide and 1.8 parts by weight of aniline in xylene is admixed with xylene in the potassium formanilide maker to bring the total to 247.2 parts by weight. There is then added the entire charge of potassium butoxide as rapidly as possible. Little or no heat is generated by this step. The reactor is closed, vacuum is applied, and the absolute pressure is adjusted to 100±5 mm. Heat is applied to the reactor to effect distillation. The initial distillate occurs at a pot temperature of about 74° C., giving a vapor temperature of 65° C. The vapor temperature rises rapidly to 68°–70° and remains relatively constant until the butanol content in the pot becomes low. Initially, all of the reactants are in solution. About midway in the distillation, potassium formanilide begins to precipitate. In the final stages, the batch is a thick slurry. As the butanol is depleted, the vapor temperature rises about 10° C. to 78°–80° C. and the pot temperature to about 85° C. As soon as such temperature rise occurs, refractive indices are determined on samples of the distillate. Butanol removal is complete when a refractive index of $N_D25$ 1.496 is reached. The slurry contains 103 parts by weight potassium formanilide, 30.2 parts by weight formanilide, 2.1 parts by weight aniline, 0.3 parts by weight of potassium formate and 272.0 parts by weight xylene. The potassium formanilide slurry is now ready for the condensation with p-nitrochlorobenzene to prepare 4-nitrodiphenylamine.

4-Nitrodiphenylamine

To the aforedescribed slurry of 103.0 parts by weight of potassium formanilide 30.2 parts by weight of formanilide, 2.1 parts by weight of aniline and 0.3 parts by weight potassium formate in 272.0 parts by weight of xylene is added 78.5 parts by weight of p-nitrochlorobenzene at 75°±5° C. The solution is heated to reflux under a 5-plate column with a take-off allowing sampling of the overhead between the reactor and column. The pot temperature is 145°±5° C. at reflux. The reaction begins at a batch temperature of 120°±10° C., as indicated by the evolution of carbon monoxide accompanied by a color change of the batch from yellow to deep red. As soon as heatup is complete and the reflux is established, forward flow of the overhead is begun at a rate sufficient to remove 200 parts by weight of xylene. When this is accomplished, the batch temperature is 162°±3° C. and p-nitrochlorobenzene conversion is over 90%. The endpoint of the reaction is indicated when the para-nitrochlorobenzene content is less than about 0.01%. If necessary, a hold period at the upper batch temperature is used to reach the endpoint. The time required is about 3±0.5 hours. After completion of the reaction, the reaction mass is transferred to a washing vessel and washed twice with 270 parts by weight of hot water. The washed oil layer contains 100.0 parts by weight (about 94% yield) of 4-nitrodiphenylamine, no p-nitrochlorobenzene, 10.4 parts by weight of by-products, 16.3 parts by weight of aniline, 25.3 parts by weight of formanilide and 72.0 parts by weight of xylene. From 225.0 parts by weight of the washed oil, there is recovered approximately 90 wt. % of the 4-nitrodiphenylamine by crystallization, the difference being eventually recovered after xylene, aniline and formanilide have been separated and recycled to the system.

EXAMPLE 4

This example illustrates the preparation of 4-nitrodiphenylamine using, without isolation, potassium formanilide in formanilide made from aqueous sodium hydroxide and dehydrated below reaction temperature in the presence of p-nitrochlorobenzene. The presence of p-nitrochlorobenzene is advantageous, even if not subsequently employed as a reactant, because it reduces foaming in making potassium formanilide. The mole ratio is 0.5 mole of formanilide and 1.5 mole of potassium formanilide per mole of p-nitrochlorobenzene.

Formanilide

The input formanilide batch may be prepared as follows: aniline and formic acid are reacted to form formanilide and water. The reaction is carried out by charging aniline and xylene into a reaction vessel fitted with a moisture separator and heating to 45°–50° C. Formic acid is then added slowly. The exothermic formation of aniline formate will raise the batch temperature to about 80°–90° C. The mixture is held at this temperature for a one-hour hold period. The temperature is then slowly increased and water is collected by azeotropic distillation. The batch temperature is about 165° C. when water removal is essentially complete. Heating is continued and xylene is gently refluxed to the moisture separator. Additional water and formic acid are collected in the separator until the endpoint is determined by conductivity measurement or by analysis. The final batch temperature is about 165°–170° C. The resulting formanilide in xylene solution in the pot is ready for conversion to potassium formanilide and condensation of the latter with p-nitrochlorobenzene.

Potassium Formanilide

The potassium formanilide and condensation reactions are run in a stainless steel reactor which is equipped with mechanical agitation and overhead system which condenses the overhead vapors and allows separation of water, the xylene being returned to the reactor. There is charged to such reactor 162.2±1.3 parts by weight of the aforedescribed formanilide batch containing 122.7±1.0 parts by weight of formanilide. There are also added 79.5±0.5 parts by weight of p-nitrochlorobenzene and xylene to make up a total charge of 134.8±3 parts by weight. The system is closed and the reactor pressure reduced to 65±2 mm Hg. Heating is adjusted to heat the reactor charge at 4° C./min. When the reactor charge mass temperature is 60° C., but before the temperature exceeds 65° C., there is begun a steady, monitored feed of 85.9±0.5 parts by weight of 50% KOH at a rate of 2.8±0.3 parts by weight per minute. This gives a KOH charge time of 30 to 33 minutes. The temperature does not exceed 75° C. during the KOH feed. Heating is then adjusted to again heat the reactor charge at 4° C./min. Boilup of xylene and water begins with the start of the KOH feed and continues after the KOH feed is complete until the monitored heat input is sufficient to boil up to 56.3 parts by weight of water plus 900.8 parts by weight of xylene. The water is separated from the condenser output and the xylene is returned to the reactor. The reaction mass temperature does not exceed 90° C. during this dehydration.

4-Nitrodiphenylamine

The reactor pressure is increased to atmospheric while maintaining the aforesaid rate of heating. The potassium formanilide reaction mass is heated to reflux temperature which is near 150° C. at atmospheric pressure. When reflux is attained, the forward distillate is stripped sufficient to raise the reaction mass temperature to 163°–165° C. and 83.7 parts by weight of distillate, containing 80.8 parts by weight of xylene is removed. The aforesaid temperature is held for 75 minutes and the reaction mass cooled and quenched with 105.6 parts by weight of water. After washing the reaction mass with hot water at 90°–95° C., the 4-nitrodiphenylamine is recovered by recrystallization. The foregoing procedure gives yields of 90–95% and conversion of 98–100%.

EXAMPLE 5

This example illustrates the preparation of 4-nitrodiphenylamine using without isolation, cesium formanilide in formanilide made from cesium hydroxide. The mole ratio is 0.4 mole of formanilide and 1.25 mole of cesium formanilide per mole of p-nitrochlorobenzene.

Cesium Formanilide

The procedure described by Kitchens for preparing the potassium salt of ortho formotoluidide (U.S. Pat. No. 2,442,952, June 8, 1948) can be successfully adapted to the preparation of cesium formanilide intermediate. To 75 parts by weight (0.5 mole) of cesium hydroxide in 100 parts by weight of benzene there is added 61.5 parts by weight (0.51 mole) of formanilide dissolved in 100 parts by weight of benzene over a period of about 4¾ hours at 78°–80° C. while separating by-product water. Heating at 80°–80.5° C. is continued for about four hours to collect a total of about 12.4 parts by weight of water. At this temperature, the cesium formanilide is molten.

4-Nitrodiphenylamine

To the resulting slurry of cesium formanilide is added 63 parts by weight (0.4 mole) of p-nitrochlorobenzene, 7.9 parts by weight (0.065 mole) of formanilide and 200 parts by weight of xylene. The reaction mixture is heated to about 140° C. over a period of about an hour and heating continued at 140°–146° for about 3 hours. Gas evolution increases rapidly at about 121° C. and continues throughout most of the heating period. During the heating, the major proportion of the hydrocarbon solvent is removed as distillate. The reaction mixture is washed with water and then xylene is added at 90° C. The organic layer is separated and dried. From the organic layer 54.6 parts by weight (0.255 mole) of 4-nitrodiphenylamine is isolated by crystallization. From the brown mother liquor another 0.041 moles is obtained. The yield is 74.1% and conversion 80.3%.

Examples 6–10 illustrate the preparation of substituted 4-nitrodiphenylamines using without isolation a potassium salt of the corresponding substituted formanilide in the substituted formanilide the mole ratio being 0.65 mole of substituted formanilide and 1.2 moles of its potassium salt per mole of p-nitrochlorobenzene.

EXAMPLE 6

2-Methyl-4-Nitrodiphenylamine

To prepare 2-methyl formanilide 321 parts by weight (3.0 mole) o-toluidine is heated to 90° C. and to it is added under reflux condition 147 parts by weight (3.1 mole) of 97% formic acid at 90°–97° C. over a period of about 40 minutes. A water trap is then installed and heating continued at 104°–118° C. for about 5 hours while collecting water. After about one hour, 185 parts by weight of toluene is added. The reaction mass is cooled, crystallization induced and heptane added slowly under cooling. The violet solid which forms is separated by filtration and dried to give a 97% yield of 2-methyl formanilide.

Into a reactor is charged 29.7 parts by weight (0.22 mole) of 2-methyl formanilide prepared as described above, 69.9 parts by weight (0.2 mole) of 20% potassium methylate in methanol and about 170 parts by weight of xylene. The mixture is heated for about two hours at about 50°–78° C. at reduced pressure while collecting distillate. Toluene is added to maintain the liquid volume of the reaction mixture. The resulting xylene slurry of potassium 2-methyl formanilide substantially free from methanol is cooled to 50° C. and mixed with 24.2 parts by weight (0.154 mole) of paranitrochlorobenzene and 10.4 parts by weight (0.077 mole) of 2-methyl formanilide. The resulting mixture is heated and stirred under atmospheric pressure for about 1½ hours at 130°–149° C. Gas evolution starts at about 124° C. The hot reaction mixture is quenched with 85 parts by weight of xylene and 100 parts by weight of 90° C. water gradually added under stirring. The organic layer is separated and washed a second time with 100 parts by weight of hot water. From the xylene there is recovered 2-methyl-4'-nitrodiphenylamine in yield of 97.5%. Conversion of p-nitrochlorobenzene is 100%.

EXAMPLE 7

4-Methoxy-4'-Nitrodiphenylamine

The intermediate, 4-methoxy formanilide is prepared by heating 369.6 parts by weight (3.0 mole) of para anisidine to 90° C. and adding to it 147 parts by weight (3.1 mole) of 97% formic acid over a period of 80 minutes at 95°–105° C. under reflux conditions. A water trap is then installed and heating continued at 91°–111° C. for about 5 hours while collecting water. Toluene is added to aid the removal of water. The reaction mixture is cooled, crystallization induced by scratching, and heptane added. The crystalline mass is cooled to 5° C. and filtered to obtain, after air drying 447.6 parts by weight of 4-methoxy formanilide as a purple solid.

Into a suitable reactor is charged 33.2 parts by weight (0.22 mole) of 4-methoxy formanilide prepared as described above, 69.9 parts by weight (0.2 mole) of 20% potassium methylate in methanol and 85 parts by weight of xylene. The mixture is heated and stirred at reduced pressure for 52 minutes at 54° C. while collecting a small amount of distillate. Another 85 parts by weight of xylene is added which results in some separation of a white solid. Heating is continued for an hour at 70°–78° C. and 100 mm. Hg. pressure while collecting distillate. There is then added to the methanol free residue of potassium 4-methoxy formanilide in xylene, 22.4 parts by weight (0.154 mole) of paranitrochlorobenzene and 11.6 parts by weight (0.077 mole) of 4-methoxy formanilide. The reaction mixture is heated and stirred at atmospheric pressure for about 1½ hours at 130°–149° C. The product is isolated from the reaction mixture as described in Example 7 to obtain 4-methoxy-4'-nitrodiphenylamine in a yield of 84%. Conversion of paranitrochlorobenzene is 100%.

Example 8

2-Chloro-4'-Nitrodiphenylamine

Into a suitable reactor is charged 34.2 parts by weight (0.22 mole) of 2-chloroformanilide, 69.9 parts by weight (0.2 mole) 20% potassium methylate in methanol and 85 parts by weight xylene. To form the potassium salt, the mixture is heated and stirred under reduced pressure for about two hours at 54°–78° C. while collecting distillate. During the reaction, xylene is added to maintain the liquid content of the reaction mixture. The vacuum is then released and 24.2 parts by weight (0.154 mole) of para-nitrochlorobenzene and 12.0 parts by weight (0.077 mole) 2-chloroformanilide added in one portion. The mixture is heated and stirred at atmospheric pressure for about 3 hours at 130°–185° C. From the reaction mixture 24.4 parts by weight of 2-chloro 4'-nitrodiphenylamine are obtained by work-up as disclosed in Example 7 and recrystallization from hot xylene.

Example 9

4-Chloro-4'-Nitrodiphenylamine

Into a reactor is charged 34.2 parts by weight (0.22 mole) of 4-chloroformanilide, 69.9 parts by weight (0.2 mole) 20% potassium methylate in methanol and 85 parts by weight of xylene. The mixture is stirred under reduced pressure and heated at 51°–85° C. for about one hour while collecting distillate, the liquid content to the reaction mixture being maintained by adding xylene. The vacuum is then released and 24.2 parts by weight (0.154 mole) of para-nitrochlorobenzene and 12.0 parts by weight (0.077 mole) of 4-chloroformanilide added in one portion. The mixture is heated and stirred at 70°–80° C. under 100 mm. of Hg pressure while removing xylene and then heated and stirred at 135°–158° C. under atmospheric pressure for about 2 hours. The reaction mixture is quenched with 85 parts by weight of xylene and washed with 100 parts by weight hot water. Solids crystallize out of the xylene at 90° C. after the first water wash. The mass is filtered without separating the water to obtain 31.8 parts by weight of 4-chloro-4'-nitrodiphenylamine as a brown solid. A second crop of 14.0 parts by weight separates from the filtrate.

EXAMPLE 10

4,4'-Dinitrodiphenylamine

Potassium 4-nitroformanilide is prepared by suspending in a reaction flask 83 parts by weight (0.5 mole) 4-nitroformanilide in dimethylformamide, adding to the suspension 62.2 parts by weight (0.5 mole) of 45% aqueous KOH and stirring at room temperature for ½ hour. The solid is separated by filtration washed with acetone and dehydrated in 130 parts by weight benzene to obtain 46 parts by weight of potassium 4-nitroformanilide as a bright yellow solid.

To 40.8 parts by weight of potassium 4-nitro formanilide (0.20 mole) prepared as described, there is added 21.7 parts by weight (0.154 mole) of p-nitrofluorobenzene, 12.8 parts by weight (0.077 mole) 4-nitroformanilide and 25 parts by weight of dimethylformamide. The mixture is heated to 100° C. at which temperature the reaction mixture becomes exothermic. The temperature is increased to 130° over a period of about an hour and then heated and stirred at 130°–170° C. for 85 minutes. On cooling, the reaction mixture solidifies to a bright orange cake. Hot water is added to the reaction flask and the solids washed with stirring for 30 minutes at reflux temperature. The solids are filtered, dissolved in dimethylformamide and cooled in an ice bath. There is obtained 10 parts by weight of 4,4'-dinitrodiphenyl amine mp 214°–16° C.

EXAMPLE 11

This example illustrates the preparation of 4-nitrodiphenylamine from sodium formanilide and formanilide including the preparation and isolation of the sodium formanilide intermediate as well as a suitable method for preparing sodium formanilide to be reacted without isolation. The mole ratio is 1.6 moles of formanilide and 1.3 moles of sodium formanilide per mole of p-nitrochlorobenzene.

Sodium Formanilide

To 41.6 grams of formanilide (0.35 mole) dissolved in 200 ml of xylene is added dropwise under stirring at 80° C. under about 100 mm Hg. pressure 70.2 g. of 25% by weight sodium methoxide in methanol (0.325 mole). The methanol is distilled off followed by the higher boiling solvent in vacuo at a pot temperature below about 85° C. until the refractive index of the distillate is that of xylene (1.497). The solid sodium salt is separated by filtration and protected from moisture until ready for use. To prepared sodium formanilide and formanilide for use without isolating the sodium formanilide the foregoing procedure is followed omitting the filtration step, employing the desired excess of formanilide and replacing the methanol by xylene or other suitable solvent to keep the slurry fluid. The p-nitrochlorobenzene is then added and xylene stripped out until the desired temperature is reached.

4-Nitrodiphenylamine

Into a suitable reactor is charged 78.5 parts by weight (0.5 mole) of p-nitrochlorobenzene, 93.8 parts by weight (0.65 mole) of sodium formanilide, 96 parts by weight (0.8 mole) of formanilide. The mixture is gradually heated and stirred; and, at about 134° C., evolution of carbon monoxide begins. Heating is continued until the temperature reaches 180°, at which temperature the reaction mixture becomes self-heating. Stirring is continued at 180°. After about two and one-half hours, 18 parts by weight of carbon monoxide are evolved; and reaction is stopped, xylene added, and the xylene solution washed with 250 parts by weight of water, separated from the water and cooled to 10° C. The crystals of 4-nitrodiphenylamine which form are separated by filtration and washed with a little xylene. From the mother liquor a second crop of 4-nitrodiphenylamine is recovered. The yield of 4-nitrodiphenylamine is 86% and conversion of p-nitrochlorobenzene is 96%. The presence of the formanilide reduces tertiary amine byproduct which becomes excessive in the case of reaction in dimethylformamide, for example.

EXAMPLE 12

This example illustrates the preparation of 4-nitrodiphenylamine from sodium formanilide and formanilide in a mole ratio of 0.6 moles of formanilide and 1.3 moles of sodium formanilide per mole of p-nitrochlorobenzene and demonstrates the importance of formanilide.

Reactions are carried out in a 500 ml. three-necked round bottom flask fitted with an overhead paddle stirrer, 2-plate Oldershaw column with Dean-Stark separator and condenser, thermometer, dropping funnel, and gas meter to measure the CO evolved. In each case, the basic reactants are 60.6 grams (0.385 mole) of para-nitrochlorobenzene and 70.6 grams (0.5 mole) of sodium formanilide. In Example 12, 30.6 grams (0.25 mole) of formanilide are used as reaction adjuvant to provide a ratio of 1.3 molecular proportions of sodium formanilide and 0.62 molecular proportions of formanilide per mole of para-nitrochlorobenzene. The para-nitrochlorobenzene and formanilide are heated with mixing to 90° C. and the sodium formanilide charged in one portion.

In comparative Example 12A, outside the invention, the formanilide is omitted and 10 ml. of xylene added as reaction adjuvant. In comparative Example 12B, also outside the invention, the formanilide is omitted and 50 ml. of dimethylformamide added as reaction adjuvant. The reaction masses are heated and stirred as described in the table below with the indicated results.

After the heating periods 150–200 ml. of xylene are added to quench the reactions and the resulting masses washed twice with 200 ml. portions of 90° C. water. The xylene layers are separated and cooled in an ice bath. The solid 4-nitrodiphenylamine is separated by filtration and washed with 50 ml. of cold xylene and dried. The amount of 4-nitrodiphenylamine in the mother liquor is determined by gas liquid chromatography. Also recorded are the moles of 4,4'-dinitrotriphenylamine (DNTPA) formed.

TABLE I

| Example | 12 | 12A | 12B |
|---|---|---|---|
| Adjuvant | Formanilide | xylene | dimethylformamide |
| Reaction time, minutes | 90 | 89 | 90 |
| Reaction temperature °C. | 159-171 | 162-183 | 156-159 |
| CO, liters | 8.82 | 4.4 | 6.7 |
| Yield % | 76.9 | 53.3 | 69.9 |
| Conversion % | 96.8 | 93 | 97.7 |
| Moles of DNTPA | .0047 | .0043 | .0141 |

EXAMPLE 13

This example further illustrates the special properties of potassium formanilide as a reactant. Potassium formanilide is substituted for sodium formanilide in Example 12A in equivalent proportions using the apparatus described in Example 12. Thus 60.6 g. (0.385 mole) of p-nitrochlorobenzene, 79.6 g. (0.5 mole) of potassium formanilide and 10 ml of xylene are heated under stirring and the reaction mass worked up as described in Example 12. In Example 13A the xylene is replaced by 50 ml of dimethylformamide as reaction adjuvant. The results are summarized in the table below and show that high yields are obtainable with no polar solvent. Dimethylformamide is, if anything, detrimental.

TABLE II

| Example | 13 | 13A |
|---|---|---|
| Adjuvant | xylene | dimethyl formamide |
| Reaction time, minutes | 91 | 90 |
| Reaction temperature, °C. | 150-160 | 148-167 |
| CO, liters | 7.3 | 7.2 |
| Yield % | 84.9 | 83.9 |
| Conversion | 96.9 | 99.1 |
| Moles of DNTPA | .0154 | .0199 |

EXAMPLE 14

This example illustrates the preparation of 4-nitrodiphenylamine from sodium formanilide and formanilide and illustrates reducing the evolution of carbon monoxide by addition of aniline.

The reactions are conducted by heating for 1.5 hours 0.154 molecular proportions of p-nitrochlorobenzene, 0.2 molecular proportions of sodium formanilide, (about 1.3 moles per mole of p-nitrochlorobenzene) and proportions of formanilide and aniline varying from 0.5 to 2.6 moles per mole of p-nitrochlorobenzene. The reaction temperatures, moles of formanilide and aniline per mole of p-nitrochlorobenzene (PNCB) liters of carbon monoxide evolved, percent conversion of PNCB, and yields of 4-nitrodiphenylamine are summarized in the table below. It will be noted that the presence of aniline reduces the amount of carbon monoxide evolved with equivalent results; but, as shown by comparative example 14I, cannot replace the minimum requirements of formanilide.

| Example | Temperature °C. | Formanilide moles per mole of PNCB | Aniline moles per mole of PNCB | Gas Evolution Liters | Conversion of PNCB % | Yield % |
|---|---|---|---|---|---|---|
| 14A | 170-180 | 1.30 | none | 6.1 | 95 | 87 |
| 14B | 170-180 | .65 | 0.65 | 3.9 | 100 | 89 |
| 14C | 165-174 | .50 | .5 | 3.3 | 100 | 88 |
| 14D | 165-176 | .65 | none | 4.5 | 97 | 86 |
| 14E | 175-180 | 2.60 | none | 8.2 | 100 | 96 |
| 14F | 175-179 | 1.95 | .65 | 5.7 | 100 | 96 |
| 14G | 175-178 | 1.30 | 1.30 | 3.3 | 100 | 94 |
| 14H | 175-180 | .65 | 1.95 | 1.8 | 100 | 90 |
| 14I | 175-176 | none | 2.10 | 0.3 | 82.6 | 58.6 |
| 14J* | 200-204 | .5 | none | 5.0 | 97.7 | 83.2 |
| 14K* | 161-164 | .5 | none | 4.0 | 87.3 | 79.3 |

*Prepared from a different sample of sodium formanilide than 14A-14I.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. The process which comprises forming a nitrodiarylamine by reacting a sodium, potassium, rubidium or cesium salt of the formyl derivative of an aromatic primary amine with nitrohaloarene containing halogen reactive with such salt the reaction being promoted in the case of a sodium salt with the formyl derivative of an aromatic primary amine in an amount of at least 0.4 mole per mole of nitrohaloarene.

2. The process which comprises forming a nitrodiarylamine by reacting
   (A) alkali metal salt of the formyl derivative of an aromatic primary amine wherein the alkali metal is potassium, cesium, rubidium or mixture thereof with
   (B) nitrohaloarene containing halogen reactive with said salt, the alkali metal salt being preformed.

3. The process which comprises forming a nitrodiarylamine by reacting
   (A) alkali metal salt which is alkali metal formanilide or alkali metal formanilide substituted in the benzene nucleus by one or more alkyl, alkoxy, nitro, fluoro or chloro substituents wherein the alkali metal is potassium, cesium, rubidium or mixture thereof with
   (B) nitrohalobenzene containing halogen reactive with said salt, the salt being preformed.

4. The process of claim 3, wherein the alkali metal is potassium.

5. The process of claim 3, wherein A is potassium formanilide and B is p-nitrochlorobenzene.

6. The process of making 4-nitrodiphenylamine which comprises heating a reaction mixture of potassium formanilide, formanilide and p-nitrochlorobenzene, the mole ratio of potassium formanilide being 1.0–1.5 moles per mole of p-nitrochlorobenzene and formanilide 0.25–1.0 moles per mole of p-nitrochlorobenzene.

7. The process of claim 6 wherein the potassium formanilide is generated from aqueous potassium hydroxide in the presence of p-nitrochlorobenzene, dehydrated and then reacted with the p-nitrochlorobenzene.

8. The process of claim 6 wherein the formanilide ratio is 0.25–0.65 mole per mole of p-nitrochlorobenzene.

9. The process of claim 6 conducted at 155°–165° C.

10. The process of claim 6 wherein the reaction mixture contains an inert non-polar solvent.

11. The process which comprises forming nitrodiaryl amine by reacting sodium formanilide, p-nitrochlorobenzene and a reaction-promoting amount of formanilide wherein the sodium formanilide is 1.0–1.5 moles and the formanilide 0.4–2.6 moles per mole of p-nitrochlorobenzene.

12. The process of claim 1 wherein aniline is present to reduce carbon monoxide evolution.

13. The process of claim 11 wherein the mole ratio of the formanilide to sodium formanilide is equal to or greater than one.

14. The process of claim 13 wherein the ratio of formanilide to p-nitrochlorobenzene is two or more.

* * * * *

UNITED STATES PATENT AND TRADEMARK OFFICE
CERTIFICATE OF CORRECTION

PATENT NO. : 4,187,248
DATED : February 5, 1980
INVENTOR(S) : Helmut L. Merten and Gene R. Wilder It is certified that error appears in the above-identified patent and that said Letters Patent are hereby corrected as shown below:

Column 1, line 12, the words -- 4-nitrodiphenyl amine from p-nitrochlorobenzene -- should be inserted after "of".

Column 2, line 4, "0.4-0.5" should read -- 0.4-.5 --.

Column 14, line 3, "0.5" should read -- .5 --.

Signed and Sealed this

Tenth Day of June 1980

[SEAL]

Attest:

SIDNEY A. DIAMOND

Attesting Officer

Commissioner of Patents and Trademarks